United States Patent [19]

Pierce

[11] Patent Number: 5,356,431
[45] Date of Patent: Oct. 18, 1994

[54] CONNECTIVE TISSUE STABILIZER AND METHOD OF USE

[76] Inventor: Frank C. Pierce, 3998 Belair Rd., Augusta, Ga. 30909

[21] Appl. No.: 883,645

[22] Filed: May 15, 1992

Related U.S. Application Data

[63] Continuation-in-part of Ser. No. 614,727, Nov. 16, 1990, abandoned.

[51] Int. Cl.⁵ .......................... A61F 2/02; A61F 2/18; A61F 2/08; A01K 29/00
[52] U.S. Cl. ...................... 623/11; 119/814; 623/10; 623/13
[58] Field of Search ................ 623/10–14; 119/96

[56] References Cited

U.S. PATENT DOCUMENTS

| | | | |
|---|---|---|---|
| 2,587,966 | 3/1952 | Cleary | 119/96 |
| 2,671,444 | 3/1954 | Pease, Jr. | 623/14 X |
| 3,608,095 | 9/1971 | Barry | 623/15 |
| 3,646,615 | 3/1972 | Ness | 623/14 |
| 3,805,300 | 4/1974 | Tascon-Alonso et al. | 623/13 |
| 3,858,247 | 1/1975 | Bauman | 623/15 |
| 3,970,080 | 7/1976 | White | 119/96 X |
| 4,010,494 | 3/1977 | Sauer | 623/10 |
| 4,147,164 | 4/1979 | Behney | 623/10 X |
| 4,148,279 | 4/1979 | Hoytt | 119/96 |
| 4,221,189 | 9/1980 | Olvera | 119/96 |
| 4,250,875 | 2/1981 | Marsh et al. | 119/96 X |
| 4,252,110 | 2/1981 | Behney | 623/10 X |
| 4,320,722 | 3/1982 | Glassman et al. | 119/96 |
| 4,475,547 | 10/1984 | Cox | 119/96 X |

*Primary Examiner*—David Isabella
*Assistant Examiner*—Elizabeth M. Burke
*Attorney, Agent, or Firm*—Hopkins & Thomas

[57] ABSTRACT

A connective tissue stabilizer for use in medical applications to stabilize and support cartilage, and the like is disclosed, the stabilizer having a body portion with a flattened end. The flattened end has an eye for receiving sutures or the like. The body portion generally corresponds to the shape of the tissue to be supported and may be removed after healing or left in place indefinitely.

10 Claims, 2 Drawing Sheets

CONNECTIVE TISSUE STABILIZER AND METHOD OF USE

This application is a continuation in part of co-pending application Ser. No. 07/614,727, filed Nov. 16, 1990 now abandoned.

BACKGROUND OF THE INVENTION

Connective tissues in the bodies of humans and animals include cartilage, ligaments, tendons, muscles etc. Of these, cartilage is a tough, fibrous tissue normally attached to the articular surfaces of bones. Cartilage also makes up the majority of the ear and nose structures. In cases of injury or reconstructive surgical procedures, new cartilaginous material is slowly produced by the body providing the injured is relatively young, thus "knitting" the injured or separated areas together.

While the healing process is taking place, the affected tissues are normally supported in some suitable manner, such as with tape, splints, plaster or other type casts, etc. In cases where no new cartilaginous material is being produced, due to age or other factors, supporting means may be permanently installed or attached.

One example of a situation where support is required after a surgical procedure is that where a dog has its ears cropped. The normal, large, floppy rounded ear is cut to substantially a triangular shape. After the surgery, the ears are taped or otherwise held in an upright position to train the muscles which control ear movement and stabilize the cartilage. After a suitable length of time, the tape or supports are removed and the muscle structure is relied upon to move the ears between upright and resting or laid back positions. Ear cropping is quite common with certain breeds to, for example, make the animal seem more alert, to alter the animals appearance for show purposes, to make the animal look fierce, and/or to help keep the ears cleaner.

Taping or otherwise securing the ears or, for that matter, other parts of the body, may lead to serious and, in some cases, injurious consequences. For example, taping a dogs' ears may create an anaerobic environment and resultant decay below the tape. The adhesive itself may strip off hair or even hide when removed. For all the problems, there is also the possibility that the taping or other means may not work and further surgery or other measures may be necessitated.

SUMMARY OF THE INVENTION

It is, therefore, one of the principal objects of this invention to simplify the stabilization of connective tissue, utilizing an implant that is secured subcutaneously or within the tissue itself in the affected area and which is a more humane procedure than prior art methods.

Another object of the present invention is to hasten recovery time after surgery and to provide an implant that may be easily removed upon recovery or which may be left in place as a permanent stabilizer.

A further object of present invention is to provide an implant that is easily installed by the surgeon, is inexpensive to produce, and is durable to provide a long service life.

These and other objects are attained by the present invention which relates to a stabilizing member used as a subcutaneous or internal implant. The member may vary in shape and dimensions depending on the intended use thereof. The stabilizing member is preferably formed from a relatively rigid material which; however, has a degree of flexibility. The material should also be capable of sterilization and be hypo-allergenic so as to be non-reactive with body tissues or fluids. Means are also provided for securing the member in place, such means normally being combined with sutures.

Various additional objects and advantages of the present invention will become apparent from the below description, with reference to the accompanying drawings.

DETAILED DESCRIPTION OF THE PREFERRED EMBODIMENT

Figure 1A:
FIG. 1a is an enlarged, partial perspective view of one end of a first embodiment of the present invention.
Figure 1B:
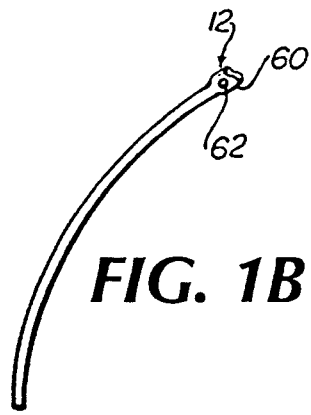
FIG. 1b is a perspective view of the first embodiment of the present invention shown in the preceding figure.

Referring now more specifically to the drawings, and to FIG. 1 in particular, numeral 10 designates generally the present connective tissue stabilizer. While alternate embodiments are contemplated and are discussed in detail hereinbelow, a preferred embodiment comprises an elongated rod member having at least one end 12 configured to receive securing means such as a suture or sutures. End 12 may also include aligning means for maintaining the securing means in a selected position with regard to the stabilizer 10 and the supported tissue, the aligning means comprising one or more grooves 14 or similar means. The stabilizer is composed of a suitable hypo-allergenic, nonreactive material such as polyethylene or other material. A material which has proven effective is a plastic monofilament rod means that is substantially rigid throughout its length. The rod means may be rounded, oval, ovoid, rectilinear, flattened, etc.

This provides the function of stability in use as the present stabilizer is, by definition placed so as to resist forces tending to cause motion, forces from muscles and the like, for example. This function of stability is also opposite from prior art devices which serve as replacement ligaments or tendon prostheses, such as those shown in U.S. Pat. No. 4,917,700; 4,946,377; and/or 4,665,951. The embodiment shown in FIG. 1 is designed as an implant for a dog's ear and is appropriately shaped to approximately the same curvature as the ear, in this instance, concave. It is important to note; however, that once the present stabilizer is formed into the particular shape, it retains substantially that shape and in this case, is a substantially rigid concave-shaped stabilizer. Thus, while the ear can move or be moved, the implant has shape memory and substantial rigidity which causes the ear or other supported tissue to return to the desired orientation and configuration in generally axial alignment with the stabilizer. Alternate shapes and dimensions of the implant are possible and will vary depending on the ultimate use of the stabilizer. Such alternate embodiments are considered to be within the scope of the present invention.

Figure 2:
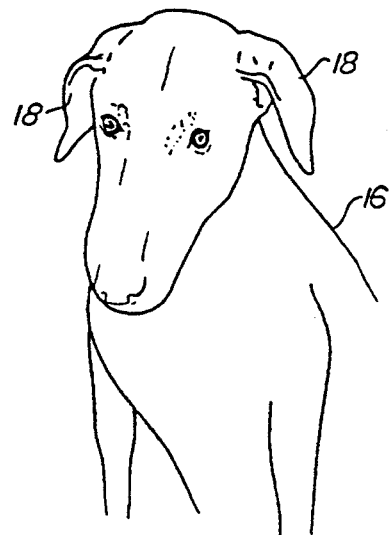
FIG. 2 is a partial perspective view showing a dog prior to having the ears cropped.
Figure 3:
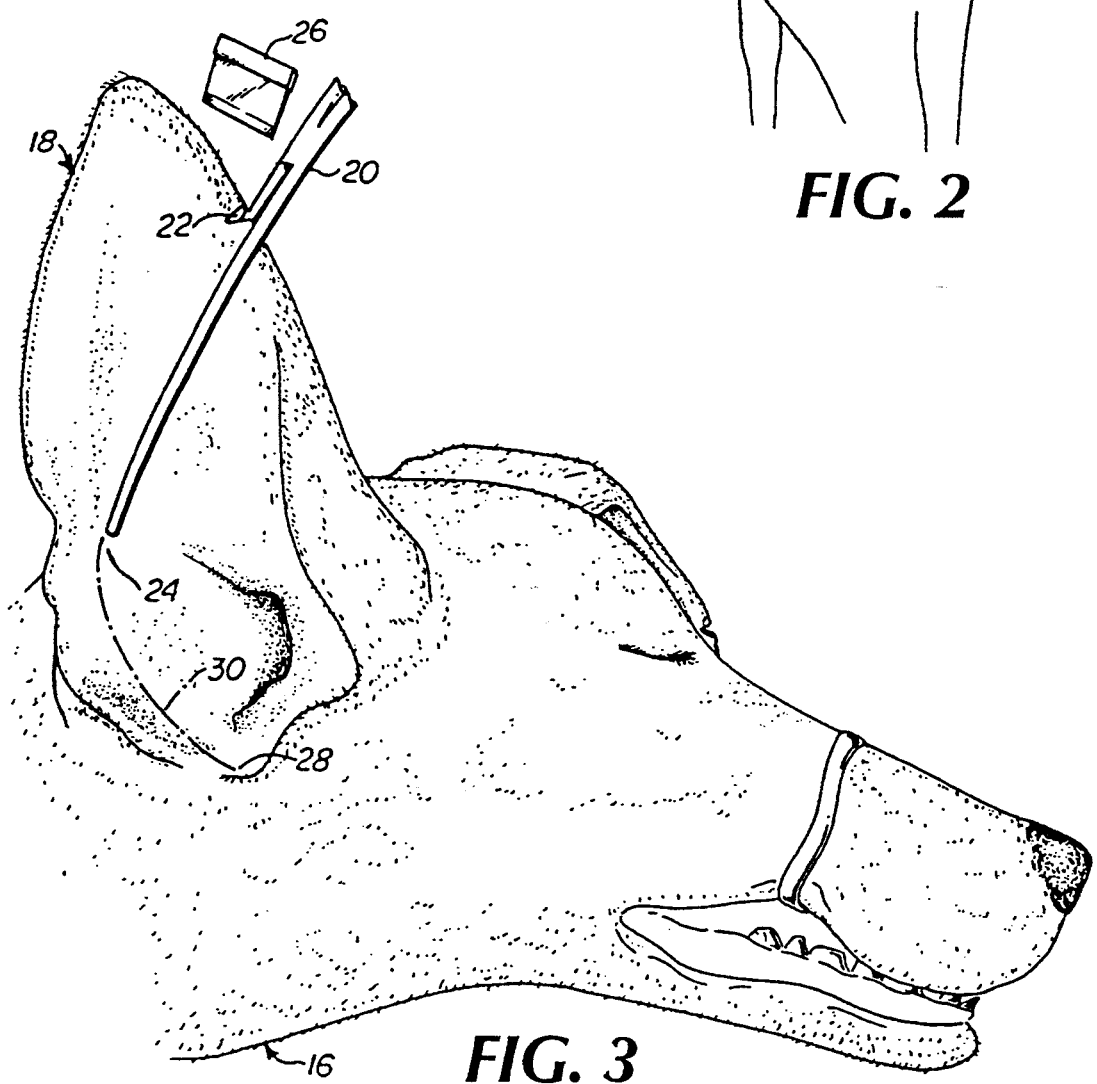
FIG. 3 is a partial perspective view illustrating one of the initial steps in trimming an ear.

Referring to FIG. 2, a dog is illustrated with floppy ears that are to be cropped, a common procedure with certain breeds such as Doberman Pinschers, Bouvier de Flandres, Boxers, and others. Following is a brief discussion of the procedure. The dog 16 is anaesthetized and the ears 18 are shaved and surgically prepped. A fenestrated drape (not shown) is placed over the dog allowing the exposure of both ears with the dog in ventral recumbency. The ears are placed in exact opposition for measurement purposes and to determine where the cut will be made. The ears are then trimmed one at a time, an instrument such as a Doyen intestinal hemostatic forceps 20 being placed on the ear from a starting cut 22 to the most proximal aspect of the medial process of the antitragus, designated generally by numeral 24. The forceps serve as a guide for trimming the ear, as shown in FIG. 3, the cut being made with a razor 26, scalpel, or similar instrument. The ear is then cut to the level of the lateral crus of the helix 28, the cut being normally made free hand with scissors, and generally along line 30.

Figure 4:
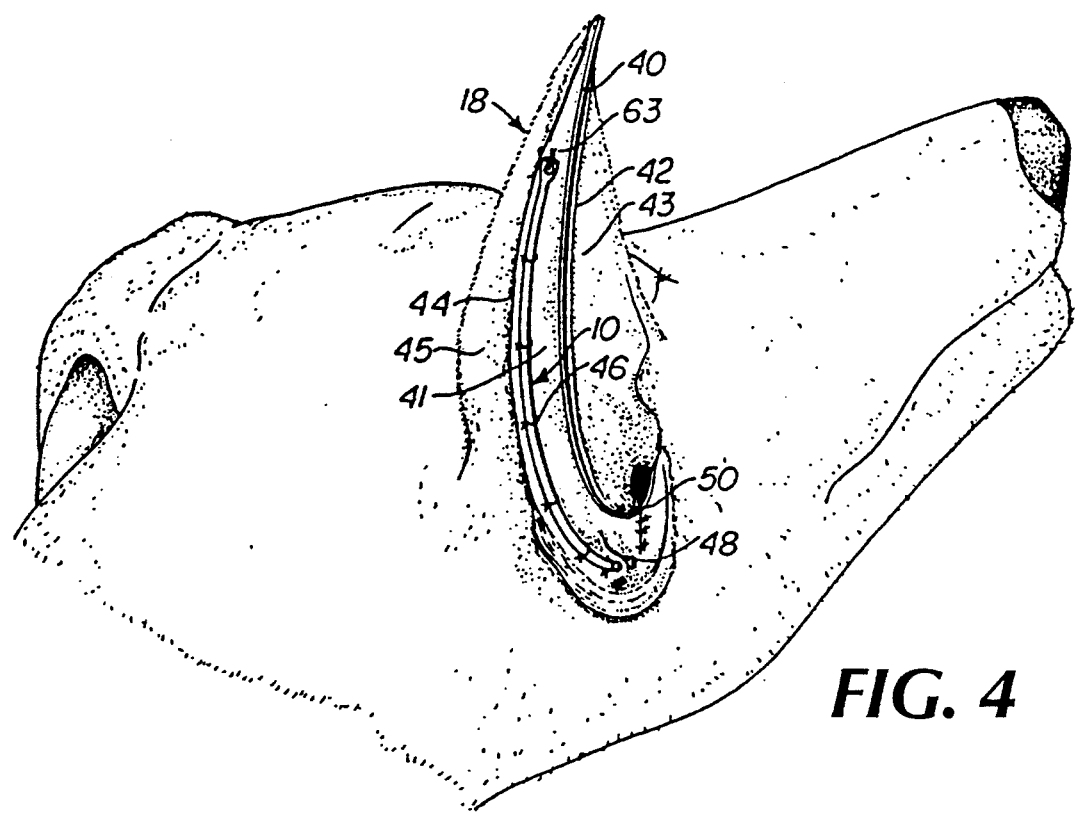
FIG. 4 is a partial perspective view illustrating the present stabilizer in place adjacent the ear cartilage and affixed to cartilage with sutures.

Referring now to FIG. 4, numeral 40 designates the edge of the trimmed cartilage, numeral 42 is the edge of the skin 43 of the inner side of the ear 18, and numeral 44 is the edge of the skin 45 of the medial or outer, shaved side of the ear. The skin 45 of the medial portion of the ear is undermined for approximately three-fourths the length of the cut ear margin to a depth of approximately one-fourth of an inch.

The present stabilizer 10 or implant is placed adjacent the outboard side of the trimmed cartilage and is first affixed at the approximate center thereof with a suitable securing means such as single monofilament 3-0 or 2-0 Ethilon suture material. The suture 46 is passed through the cartilage 41 and around the stabilizer 10 and is secured with a single surgeon's knot.

The stabilizer is then adjusted axially to a height which affords the maximum stand potential for the ear. The distal, or lower portion; however, should not be either above or below the natural indention or depression 48 below the tragus 50. Affixation of this distal end is designed such that the end is affixed to the depression or depressed cartilage 48, which allows for a more upright ear. Due to the substantially rigid nature of the present stabilizer, it will be readily apparent that inward fixation of the distal end of the stabilizer causes a corresponding outward bias of the opposite, proximal end. Thus, the present stabilizer has sufficient flexibility to be manipulated during the fixation thereof, but once secured, the stabilizer maintains the supported tissue in its preselected or desired position.

The proximal or upper end 60 is flattened and includes an aperture or eye 62 through which a suture 63 is placed. The upper end, while normally flattened, may be configured without an aperture providing it is configured to hold a suture or other securing means to prevent axial movement of the stabilizer. The flattened or beveled portion facilitates the placement of a suture through the aperture or eye as it is easily located with the needle and prevents the needle from slipping sideways. The suture is passed through the eye and tied above the proximal end, toward the tip of the ear the suture lying within the groove 14. This maintains the implant in the selected position for as long as it remains in place. While shown with a single groove, a plurality of grooves may be provided, and may either extend axially or be disposed angularly or normal to the longitudinal axis of the implant. After this primary affixation of the ends and center portion of the implant, secondary affixation is placed as needed, normally at regular intervals, to ensure substantially complete cartilage/implant contact.

Figure 5:
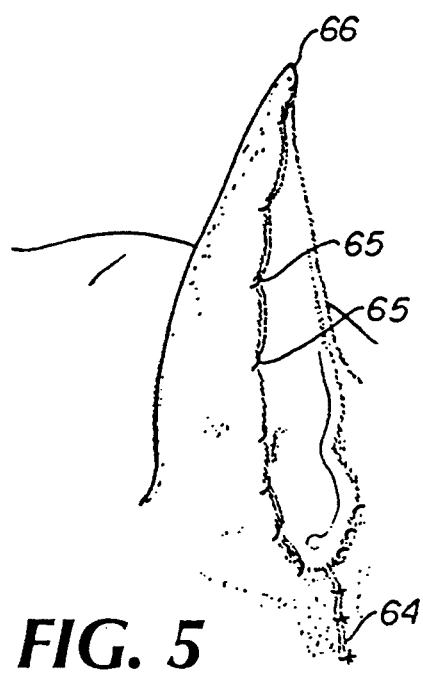
FIG. 5 is a partial perspective view illustrating the sutured ear with the stabilizer in place.

The knots securing the implant are rotated over caudally or in opposition to the supported cartilage and normally away from the cut edges to prevent their protrusion against the skin. With the implant securely in place, the inner and outer edges of the skin, 42 and 44, respectively, are pulled together. The lower portion of the ear below the tragus is sutured together as at 64. A continuous suture 65 is begun at this point, the outside edge 44 of the skin being pulled over the edge 40 of the cartilage and sutured to the inner edge 42. The pattern is continued until the entire ear is sutured, ending at the upper end 66, as shown in FIG. 5. The continuous suture is not tied, but remains free to allow for swelling and slight movement of the sutures, which occurs naturally during the healing process.

In the majority of cases with young animals, the present stabilizer or implant is removed approximately two to four weeks after surgery. During this period of time, the muscles of the ear develop the necessary capacity and training to hold the ear erect when the animal is alerted. The implant is easily removed by cutting the suture which extends through the eye 62, access being gained through a small incision. The stabilizer or implant is then simply slid upwardly and out of the ear. This is a distinct and major advantage with the present invention since only a single suture needs to be cut, the procedure is done with a local anesthetic, and there is minimal disturbance or disruption of the now-aligned tissue. The implant, while generally in axial alignment with the supported tissue is also normally disposed across the conformational defect that is being corrected. This supplements weak muscles so that the muscles can, in conjunction with the stabilizer, maintain the supported tissue in the desired position, either permanently, or until the muscles develop the necessary strength to maintain the desired position.

In some cases, i.e., where cartilage damage has occurred, the implant may be left in place indefinitely, due to its non-reactive and unobtrusive nature. The present implant and method promotes better and quicker healing, as the ear and portions of the head need not be covered with tape or in some cases, automobile weatherstrip adhesive, which are used in prior art methods to secure the ears externally or with an external ear-supporting appliance in place.

The present invention thus provides certain important benefits and advantages which could not be obtained with prior art devices and/or methods. With the present implant, the ear maintains a standing orientation immediately after surgery. The elimination of the need for the tape or glue facilitates and quickens healing of the cut skin edges. Where necessary, the implant may remain in place permanently and can be adjusted axially if necessary in a relatively short and simple procedure in which the suture holding the eye is cut and replaced in a different location relative to the cartilage or other tissue. The implant may also be removed segmentally as the cartilage gains stability or "shape memory" from the implant itself. Another significant advantage the present invention provides is the ability to use the implant in animals of any age, where previously the treatment has been effective only in young animals, and to treat virtually any conformational problems which might otherwise deter the ears from standing erect.

Figure 6:
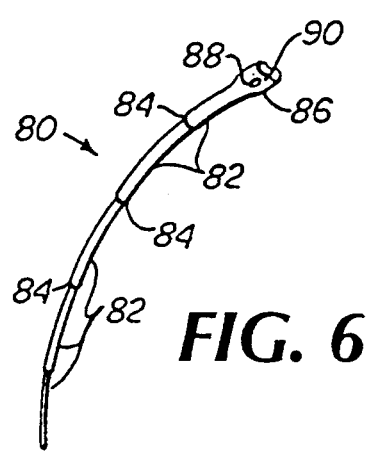
FIG. 6 is a perspective view of an alternate embodiment of the invention.

An alternate embodiment of the present invention is shown in FIG. 6. In this embodiment, the stabilizer or implant 80 has a stepped configuration, comprising a series of discrete portions which may have a gradually decreasing diameter beginning with the proximal or upper end. The individual steps 82 provide a plurality of abutments 84 against which sutures can bear to arrest axial movement of the implant. Implant 80 also includes a flattened end portion 86 having an eye 88 for receiving a securing means therethrough, such as a suture, staple, pin, etc. The end portion 88 also includes groove means 90 in which the suture or other securing means can be received for maintaining the relatively thin profile of the implant.

While the above-description has focused on the use of the present implant in veterinary medicine, the invention also has great utility in human medicine. For example, the implant may be used to stabilize a broken nose or broken cartilage in the ear structure in children or adults.

The shape and composition of the implant may also vary from that which is described in detail hereinabove. Thus, the implant may, for example, be oval, rectilinear, or substantially flat, etc., while retaining its substantial rigidity. Similarly, the length, width, and/or the diameter may vary depending on the particular application. While shown with a single eye for receiving a suture, more than one eye may be provided, either at the ends of the implant or in the body thereof particularly where the implant is designed to be permanently installed. As noted above, while plastics are generally preferred for their stability and nonreactiveness, other materials may be used, including metals, alloys of metals, hybrid materials with more than one component, and even materials which will eventually dissolve and be absorbed by the body.

Thus, while an embodiment of a connective tissue stabilizer and method of use and modifications thereof have been shown and described in detail herein, various additional changes and modifications may be made without departing from the scope of the present invention.

I claim:

1. A soft tissue stabilizer for supporting cartilage in a surgical area comprising an elongated, substantially rigid rod means having first and second ends with a body portion therebetween said body portion having a generally rounded cross section with said first end having a flattened configuration, said stabilizer also being comprised of a biocompatible hypo-allergenic material having shape memory for maintaining the stability thereof when implanted in a body, said first end including suture receiving means for anchoring said rod means to the cartilage being supported and stabilized, wherein the cartilage has a discrete shape and flexibility, and said rod means being configured to generally conform to said shape and having the flexibility of the cartilage being supported and stabilized so as to support said cartilage in a selected position in axial alignment with said stabilizer and to resist forces tending to cause motion, whereby once the stabilizer is formed into a particular shape and implanted, the supported cartilage may be moved but will return to the selected position in generally axial alignment with the stabilizer.

2. A stabilizer as defined in claim 1 in which said suture receiving means for anchoring said rod means includes a flattened portion of said first end, said flattened portion including an aperture formed therein for receiving a securing means.

3. A stabilizer as defined in claim 2 in which said flattened portion includes aligning means, said aligning means comprising groove means formed in said first end adjacent said aperture to hold at least a portion of the securing means.

4. A soft tissue stabilizer for use in medical applications for holding cartilaginous tissue in a predetermined position, said stabilizer having shaped memory and being hypo-allergenic and biocompatible with living tissues when subcutaneously implanted in a body and comprising an elongated, substantially rigid monofilament rod means having first and second ends and a body portion and having sufficient flexibility to conform to said tissue, said body portion having a substantially rounded cross-section with said first end being flattened and having means configured to receive securing means for securing said rod means to the cartilaginous tissue and maintaining said stabilizer in a selected position relative thereto by resisting forces tending to cause motion, whereby, once the stabilizer is formed into a particular shape and implanted, the cartilaginous tissue being supported may be moved but will return to the selected position in generally axial alignment with the stabilizer.

5. A stabilizer as defined in claim 4 in which said rod means is shaped to generally correspond to the cartilaginous tissue being stabilized.

6. A stabilizer as defined in claim 4 in which said means configured to receive securing means includes a substantially flattened portion at said first end, said flattened portion including an eye formed therethrough for receiving securing means.

7. A method for implanting a soft tissue stabilizer adjacent cartilaginous tissue that is to be maintained in a preselected position, said stabilizer being an elongated rod means for holding said cartilaginous tissue in said preselected position and having sufficient flexibility to generally conform to said tissue when the tissue has been placed in said preselected position and having suture receiving means formed at one end thereof for anchoring said stabilizer, comprising the steps of:
    a) creating an opening into a selected area containing the cartilaginous tissue to be stabilized;
    b) placing said stabilizer generally in axial alignment with the cartilaginous tissue to be stabilized and across a conformational defect in said tissue that is being modified;
    c) securing said stabilizer substantially adjacent to the cartilaginous tissue to be supported;
    d) placing securing means in said suture receiving means for anchoring said stabilizer and around at least a portion of said stabilizer for providing substantial stabilizer contact with said cartilaginous tissue and maintaining said stabilizer in axial alignment therewith; and
    e) closing said opening with said stabilizer in place.

8. A stabilizer as defined in claim 1 in which said elongated rod means further comprises a series of discrete portions gradually decreasing in diameter beginning at said first end of said rod means.

9. A stabilizer as defined in claim 4 in which said elongated rod means further comprises a series of discrete portions gradually decreasing in diameter beginning at said first end of said rod means.

10. A stabilizer as defined in claim 7 in which said elongated rod means further comprises a series of discrete portions gradually decreasing in diameter beginning at said first end of said rod means.

* * * * *